(12) United States Patent
Brandeis (10) Patent No.: US 11,305,060 B2
(45) Date of Patent: Apr. 19, 2022

(54) ACTUATOR AND DEVICE FOR SYNCHRONIZED INJECTION AND ASPIRATION

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

( * ) Notice: Subject to any disclaimer, the term of this patent is extended or adjusted under 35 U.S.C. 154(b) by 183 days.

(21) Appl. No.: 16/626,373

(22) PCT Filed: Jun. 25, 2018

(86) PCT No.: PCT/IL2018/050697
§ 371 (c)(1),
(2) Date: Dec. 24, 2019

(87) PCT Pub. No.: WO2019/003220
PCT Pub. Date: Jan. 3, 2019

(65) Prior Publication Data
US 2020/0129695 A1    Apr. 30, 2020

Related U.S. Application Data

(60) Provisional application No. 62/524,668, filed on Jun. 26, 2017.

(51) Int. Cl.
*A61M 5/19* (2006.01)
*A61M 1/00* (2006.01)
(Continued)

(52) U.S. Cl.
CPC ............ *A61M 5/19* (2013.01); *A61M 1/0058* (2013.01); *A61M 5/3148* (2013.01);
(Continued)

(58) Field of Classification Search
CPC .... A61M 5/19; A61M 1/0058; A61M 5/3148; A61M 5/31511; A61M 5/31581; A61M 5/14212; A61M 5/14216; A61M 5/1422
See application file for complete search history.

(56) References Cited

U.S. PATENT DOCUMENTS 6,245,046 B1    6/2001  Sibbitt
6,962,576 B2   11/2005  Sibbitt
(Continued)

FOREIGN PATENT DOCUMENTS

WO   WO 2006/079004   7/2006
WO   WO 2015/052704   4/2015
WO   WO 2019/003220   1/2019

OTHER PUBLICATIONS

International Search Report and the Written Opinion dated Sep. 17, 2018 From the International Searching Authority Re. Application No. PCT/IL2018/050697. (18 Pages).

*Primary Examiner* — Brandy S Lee
*Assistant Examiner* — Hong-Van N Trinh (57) ABSTRACT

An actuator for synchronized injection and aspiration, comprising: a first rod, having a length equal to an inner length between a head of a first plunger of a first standard-size syringe and a seal of the first plunger, and having a width smaller than a gap created between the first plunger and a barrel of the first standard-size syringe; a second rod, having a length equal to an inner length between a head of a second plunger of a second standard-size syringe and a seal of the second plunger, and having a width smaller than a gap created between the second plunger and a barrel of the second standard-size syringe; a flexible connector mechanically attached to a distal end of the first rod at a first end and to a distal end of the second rod at a second end.

8 Claims, 12 Drawing Sheets

(51) Int. Cl.
*A61M 5/31* (2006.01)
*A61M 5/315* (2006.01)
(52) U.S. Cl.
CPC .... *A61M 5/31511* (2013.01); *A61M 5/31581* (2013.01); *A61M 5/3137* (2013.01)

(56) References Cited

U.S. PATENT DOCUMENTS

2007/0016144 A1* 1/2007 Sibbitt, Jr. ......... A61M 5/31511
604/218
2010/0100033 A1 4/2010 Fojtik
2010/0106081 A1 4/2010 Brandeis

* cited by examiner

ACTUATOR AND DEVICE FOR SYNCHRONIZED INJECTION AND ASPIRATION

RELATED APPLICATIONS

This application is a National Phase of PCT Patent Application No. PCT/IL2018/050697 having International filing date of Jun. 25, 2018, which claims the benefit of priority under 35 USC § 119(e) of U.S. Provisional Patent Application No. 62/524,668 filed on Jun. 26, 2017. The contents of the above applications are all incorporated by reference as if fully set forth herein in their entirety.

FIELD AND BACKGROUND OF THE INVENTION

The present invention, in some embodiments thereof, relates to a device for synchronized injection and aspiration operated by one hand and, more particularly, but not exclusively, to an actuator for synchronized injection and aspiration of fluids using syringes, so that aspiration by one syringe is translated into simultaneous aspiration by the other syringe. This may be achieved with more than two reciprocating syringes.

The ratio between aspiration and injection in two or more syringes is dictated by pre-determining the inner volume of the syringes barrel. For example, the aspiration and injection ratio may be 1:1 (the use of two or more syringe barrels of same volume) or 1:2 (the use of one syringe barrel or more that are twice the volume of the other syringe barrel).

Some medical procedures involve injection of fluid into the patient, and removal of fluid from the patient. For example, treatment of an abscess may be performed by draining pus from the body cavity, and injection of saline into the cavity. The saline may be used to flush out remaining pus and other debris from the cavity. The injection and removal may be performed sequentially and iteratively by the healthcare provider, until all the pus has been removed and the cavity has been cleansed. In another example, vein ablation (e.g., of a varicose vein) may be performed by injection of a sclerosing agent into the vein, and removal of the excess sclerosant agent from the vein. The injection and aspiration may be performed in a controlled manner to help prevent spread of the agent into the rest of the vasculature.

Simultaneous aspiration may improve and/or enhance the effectiveness of a medication by reducing the dilution with blood or other body liquids, and by creating spasm, lower inner diameter vessel. Aspiration may reduce the amount of debris, tissue particles, blood clots and/or calcification particles, in the treated area.

Devices have been developed in order to make it easier for the healthcare provider to perform the injection and aspiration. Some devices include mechanically coupling the plunger of one syringe to the plunger of another syringe.

SUMMARY OF THE INVENTION

According to an aspect of some embodiments of the present invention there is provided an actuator for synchronized injection and aspiration, comprising: a first rod, having a length equal to an inner length between a head of a first plunger of a first standard-size syringe and a seal of the first plunger, and having a width smaller than a gap created between the first plunger and a barrel of the first standard-size syringe; a second rod, having a length equal to an inner length between a head of a second plunger of a second standard-size syringe and a seal of the second plunger, and having a width smaller than a gap created between the second plunger and a barrel of the second standard-size syringe; a flexible connector mechanically attached to a distal end of the first rod at a first end and to a distal end of the second rod at a second end. By pressing the plunger of the first syringe to inject, the second syringe automatically and simultaneously aspirates, enabling single-hand operation.

Optionally, the actuator further comprises an anchor for the flexible connector, supporting a distally disposed curve portion of the flexible connector and movement of the flexible connector.

Optionally, the first rod includes a first holder at a proximal end, the first holder is detachably mechanically coupled to the first plunger; and the second rod includes a second holder at a proximal end, the second holder is detachably mechanically coupled to the second plunger.

Optionally, the first rod and the second rod are tubes, and the flexible connector is a sting inserted into the tubes.

Optionally, the actuator further comprises a one-way mechanism which allows the flexible connector to move only in one direction.

Optionally, the first rod and the second rod are having a profile with a 90 degrees corner, to fit within an X-shaped profile of plungers.

According to some embodiments of the invention there is provided a device comprising the actuator, further comprising: a housing having syringe mounts for holding the first standard-size syringe and the second standard-size syringe.

According to some embodiments of the invention there is provided a device comprising the actuator, further comprising: a grip; and a trigger coupled to a pushing rod which pushes the first plunger.

According to an aspect of some embodiments of the present invention there is provided a method for synchronized injection and aspiration, comprising: distally displacing a first plunger of a first standard-size syringe to inject fluid from the first standard-size syringe; distally displacing a first rod, the rod having a length equal to an inner length between a head of the first plunger and a seal of the first plunger, and having a width smaller than a gap created between the first plunger and a barrel of the first standard-size syringe; distally displacing a first end of a flexible connector which is mechanically attached to a distal end of the first rod is distally displaced; proximally displacing a second end of the flexible connector which is mechanically attached to a distal end of a second rod; proximally displacing a second rod, the second rod having a length equal to an inner length between a head of a second plunger of a second standard-size syringe and a seal of the second plunger, and having a width smaller than a gap created between the second plunger and a barrel of the second standard-size syringe; and proximally displacing the second plunger to aspire fluid from the second standard-size syringe.

According to an aspect of some embodiments of the present invention there is provided a method of using a device for synchronized injection and aspiration, comprising: inserting a first standard-size syringe and a second standard-size syringe into syringe mounts of a hosing of the device; positioning a first rod adjacent to a first plunger of the first standard-size syringe, so the first rod is held by a head of the first plunger at a proximal end and by a seal of the first plunger at a distal end; positioning a second rod adjacent to a second plunger of the second standard-size syringe, so the second rod is held by a head of the second plunger at a proximal end and by a seal of the second plunger at a distal end; wherein a flexible connector is mechanically attached to a distal end of the first rod at a first end and to a distal end of the second rod at a second end; and pushing the first plunger to inject fluid from the first standard-size syringe, while aspirating fluid from the standard-size syringe.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to a device for synchronized injection and aspiration and, more particularly, but not exclusively, to an actuator for synchronized injection and aspiration of fluids using syringes.

According to some embodiments of the present invention, there is provided an actuator which includes two or more rods, connected by at least one flexible connector. In use, each rod is adjacent to a plunger of a one syringe, held by the head and seal of the plunger, so the end of the rods connected by the flexible connector, are next to the seal of the plunger. When the plunger of one syringe is pushed, the rod pulls the other rod, using the flexible connector, and the plunger of the other syringe is pulled.

The mechanism is structured and arranged to automatically translate a movement direction of the plunger of the first syringe (i.e., injection) into an opposite movement direction of the plunger of the second syringe (i.e., aspiration). Optionally, the opposite movements are parallel. Optionally, the mechanism is arranged so that insertion of the first plunger further into the barrel of the first syringe is synchronized with extraction of the second plunger from the second barrel of the second syringe, thereby injection from the first syringe is synchronized with aspiration into the second syringe. Advantageously, by pressing the plunger of the first syringe to inject, the second syringe automatically and simultaneously aspirates, enabling single-hand operation.

Synchronized injection and aspiration may be used, for example, for medical and/or veterinarian purposes. For example: the need for simultaneous injection and removal of fluids, the need for maintaining pressure within a cavity (substantially equal insertion and removal of fluid maintains the pressure within a cavity relatively constant), the need to quickly remove harmful drugs from the body after local action and/or the need to mix two or more liquids in the target body. Examples of procedures include: draining and flushing-out of an abscess, injection of therapeutics into a body cavity that needs to be maintained at a constant pressure (e.g. joint space), injection of sclerosing agents for vein ablation and removal of the agent to prevent the agent from reaching circulation.

According to some embodiments of the present invention, there is provided a device which includes the actuator and also includes a housing and/or mounts for the syringes. Optionally, the device is a handheld device sized and/or shaped to fit within the palm of one hand. Advantageously, simultaneous synchronized injection and aspiration may be performed single handedly. Optionally, the device is pistol-shaped and also includes a grip and a trigger coupled to a pushing rod which pushes one of the plungers.

Advantageously, sterility may be maintained within the fluids and/or syringes even if the device is not sterile. Advantageously, the device may be cost effective, as the device itself may be reusable, and the syringes are low cost off-the-shelf syringes. Advantageously, the device may make it easier to perform simultaneous injection and aspiration, as both movements may be performed using only one hand, instead of, for example, two operators, or one operator using both hands.

Optionally, the device comprises a one-way mechanism arranged for preventing distal displacement of the second syringe (i.e., injection by the aspiration syringe). For example, the mechanism is a ratchet. Optionally, the ratchet is coupled to the synchronization mechanism, for example, preventing reverse motion of one or more gears, moving wires or other structures. Advantageously, unsafe maneuvers are prevented or reduced by the ratchet, for example, injection of aspirated waste contents back into the patient.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
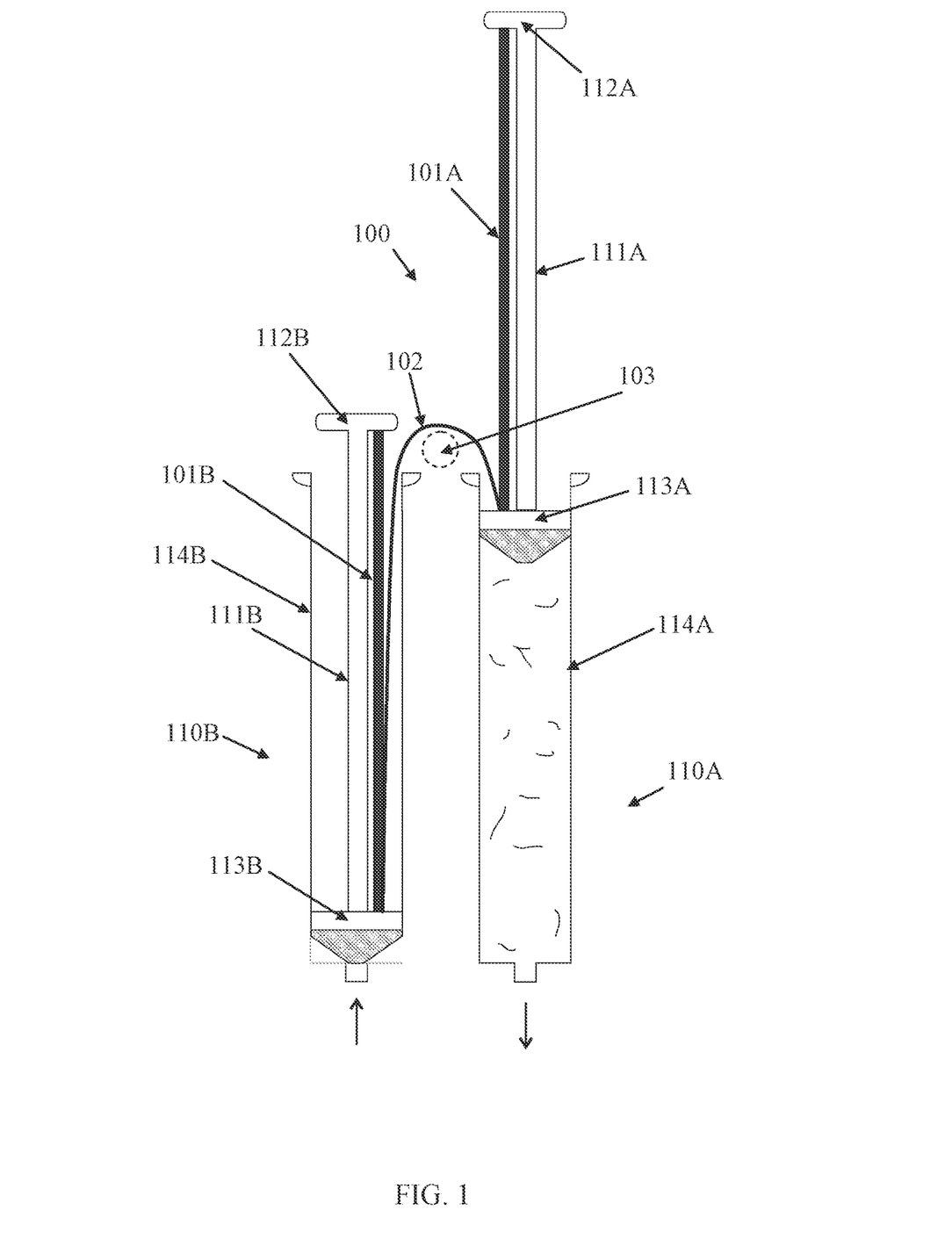
FIG. 1 is a schematic illustration of an actuator of for synchronized injection and aspiration, according to some embodiments of the present invention.

Referring now to the drawings, FIG. 1 is a schematic illustration of an actuator of for synchronized injection and aspiration, according to some embodiments of the present invention.

Actuator 100 is used with two standard-size syringes 110A-B.

Optionally, syringes 110A and 110B are of different volumes. The volume capacity of each syringe is, for example, about 1 milliliter (mL), or about 5 mL, or about 10 mL, or about 20 mL, or about 30 mL, or about 50 mL, or about 60 mL, or about 100 mL, or about 200 mL, or about 500 mL, or about 1000 mL, or other smaller, intermediate or larger volumes. The volume capacity of each syringe may be selected according to the desired ratio between injection and aspiration volumes. For example, if the ratio is 1:1, two syringes of equal sizes may be selected. In another example, if several different syringes with different drugs are used to inject, small syringes (e.g. 10 milliliters (mL)) may be used for injection, and one large syringe may be used to collect all the fluid (e.g. 60 mL).

Optionally, syringes 110A-B are off-the-shelf. Optionally, syringes 110A-B are single-use and disposable. For example, plastic disposable single use syringes commonly found in healthcare settings.

Syringes 110A-B may include any kind of syringe for injecting and/or aspiring any kind of fluid(s), including liquid, semi-liquid and/or gas.

Actuator 100 includes two rods 101A-B, each is adjacent to a plunger 111A-B of one of syringes 110A-B. Each of rods 101A-B is held by the head 112A-B of respective plunger 111A-B at the proximal end, and by the seal 113A-B of plunger 111A-B at the distal end.

To fit into syringes 110A-B, each of rods 101A-B is of a length equal to the inner length between respective head 112A-B respective seal 113A-B, of a width smaller than the gap created between respective plunger 111A-B and a respective barrel 114A-B of respective syringe 110A-B.

Optionally, the lengths of rods 101A-B are adjustable.

Rods 101A-B may be made, for example, from plastic, metal, glass and/or any other rigid material.

Actuator 100 also includes a flexible connector 102 mechanically attached to the distal end of rod 101A at one end, and to the distal end of rod 101B at the other end. Flexible connector 102 may be, for example, a cord, line, string, wire, strap, band, chain and/or any other elongated flexible member. Flexible connector 102 may be made of any kind of flexible and strong material, such as nylon.

As used herein, the term distally means away from the operator of the device. As used herein, the term proximally means towards the operator of the device. For reference, movement downward is referred to as a distal direction and movement upward is referred to as a proximal direction. Exemplary directions of fluid flow relative to actuator 100 are illustrated by arrows.

In use, injection using syringe 110A by pushing plunger 111A distally displaces rod 101A, which displaces flexible connector 102. Flexible connector 102 then pulls and proximally displaces rod 101B, which proximally displaces plunger 111B and resulting aspiration by syringe 110B.

The length of flexible connector 102 is designed for substantial linear displacement of plungers 111A-B inside barrels 114A-B, based on the sizes of syringes 110A-B.

Optionally, actuator 100 includes further one or more rods, each connected to one of the other rods by a further flexible connector. This allows using multiple syringes, some injecting and some aspirating, by only pushing or pulling one plunger.

Optionally, an anchor 103 supports flexible connector 102. Anchor 103 is supporting a distally disposed curve portion of flexible connector 102, and allows the movement of flexible connector 102. Optionally, anchor 103 is located between syringes 110A-B and is stationary relative to barrels 114A-B of syringes 110A-B.

Optionally, anchor 103 includes a tube that is held stationary relative to the syringes, for example, the tube is attached to a base. The internal diameter of the tube is larger than the outer diameter of flexible connector 102 so that flexible connector 102 is able to slide and displace inside the tube.

Optionally, anchor 103 includes one or more pulleys. Flexible connector 102 winds around the pulley(s), which allows movement of flexible connector 102 relative to the pulley(s).

Optionally, the edge(s) of one or both of barrels 114A-B functions as an anchor, so flexible connector 102 slides over them.

Optionally, actuator 100 also includes a one-way mechanism, such as a ratchet mechanism, which allows only for one-way motion of flexible connector 102 during use. For example, only injection by syringe 110A and aspiration by syringe 110B. Attempt at the opposite action (aspiration by syringe 110A and injection by syringe 110B) is opposed by the one-way mechanism. The one-way mechanism may be included in anchor 103.

Figure 2:
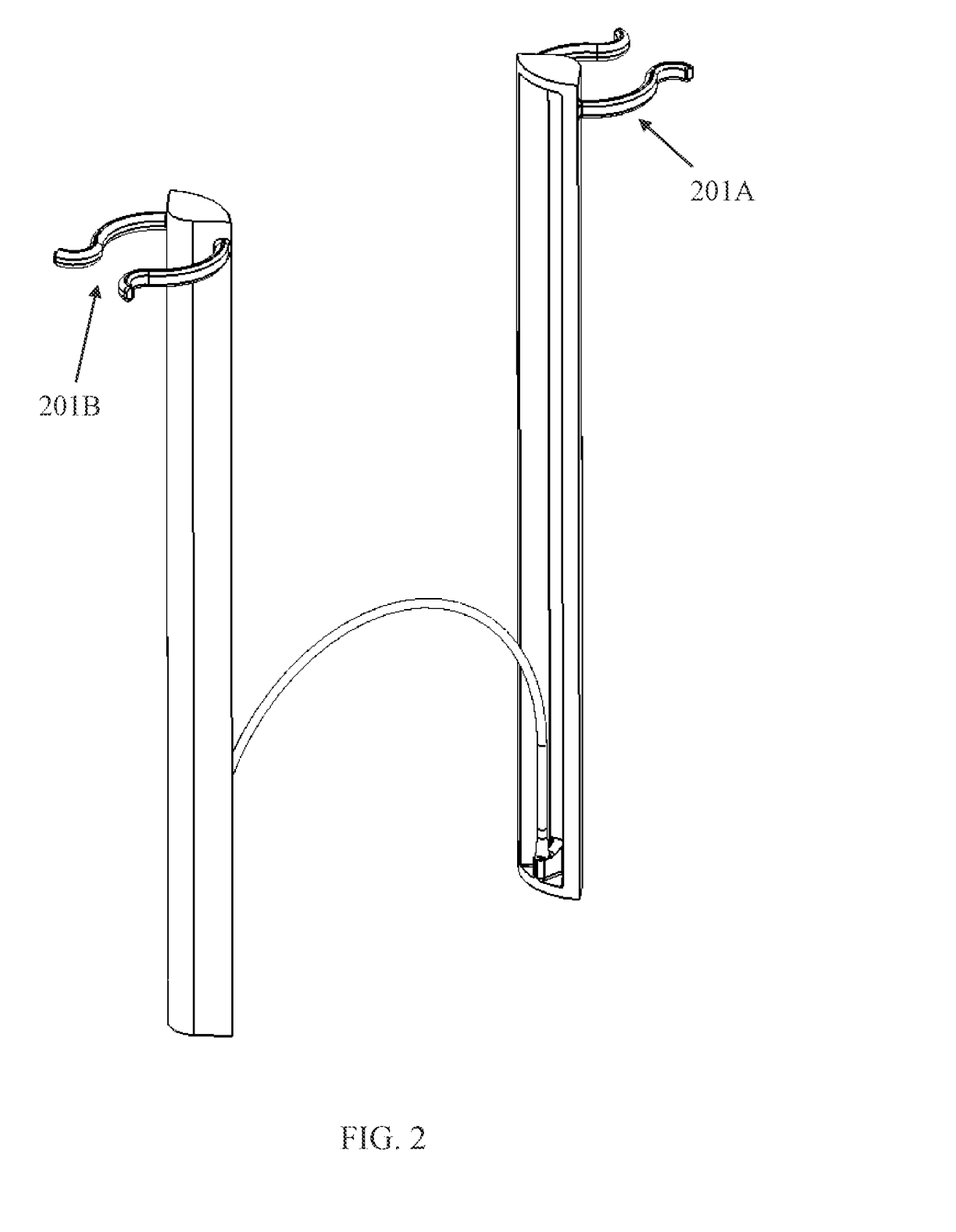
FIG. 2 is an illustration of an exemplary actuator having holders, according to some embodiments of the present invention.

Reference is now made to FIG. 2, which is an illustration of an exemplary actuator having holders, according to some embodiments of the present invention.

Optionally, actuator 100 also includes holders 201A-B for detachable mechanical coupling of rods 101A-B to plungers 111A-B, to prevent rods 101A-B from moving relative to plungers 111A-B. Optionally, holders 201A-B are attachable and detachable from syringes 110A-B so that syringes 110A-B are removable and/or replaceable. Suitable holders 201A-B include, for example, clamps, rings, elastics, crimpers, casings, or other suitable structures.

Optionally, holders 201A-B are located at the proximal end of each of rods 101A-B and designed to attach to the end portion of plungers 111A-B of syringes 1104A-B. Optionally, holders 201A-B are designed for attachment to syringes of different sizes.

Reference is now made to FIGS. 3A, 3B, 3C, 3D, 3E, 3F and 3G, which are illustrations of a device including an actuator for synchronized injection and aspiration, according to some embodiments of the present invention.

Figure 3A:
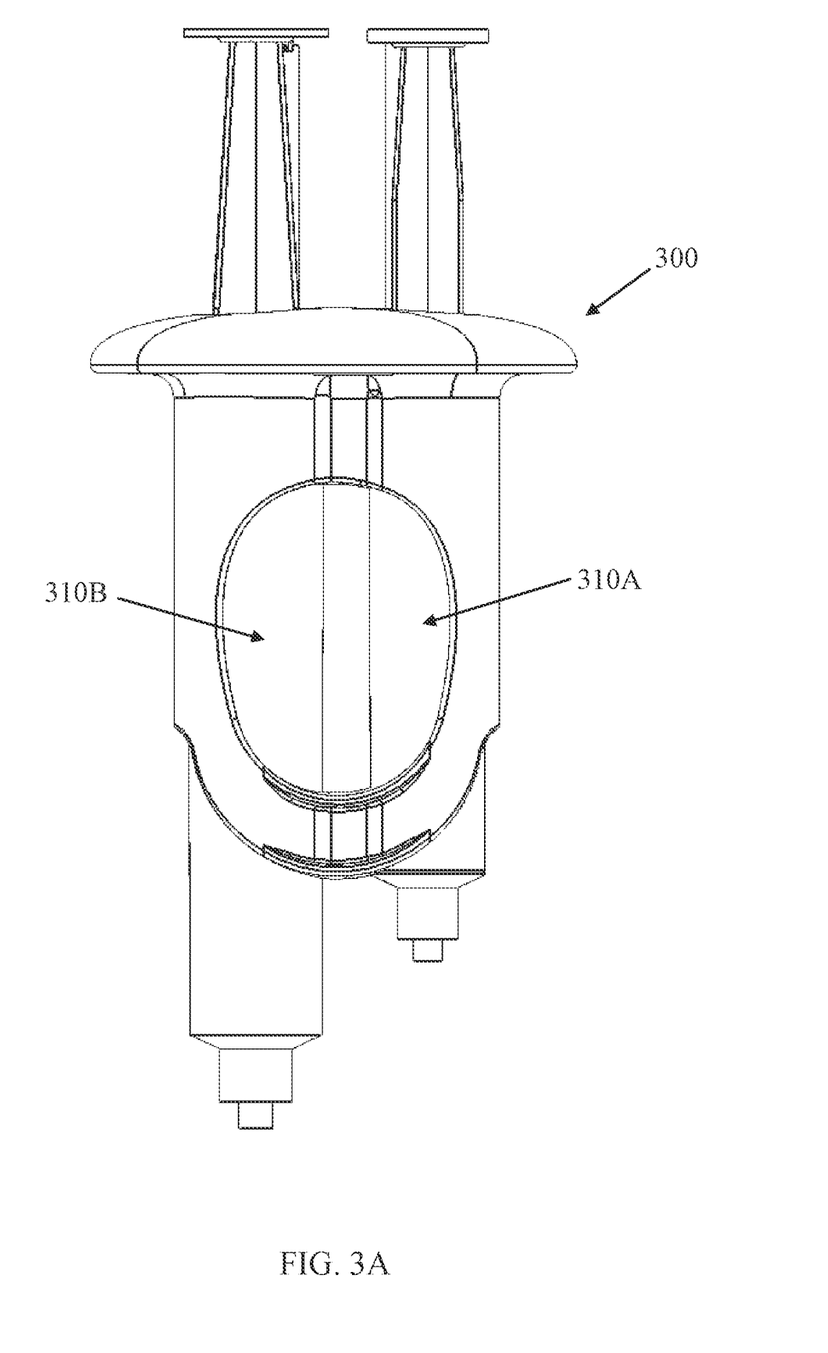
FIGS. 3A, 3B, 3C, 3D, 3E, 3F and 3G are illustrations of a device including an actuator for synchronized injection and aspiration, according to some embodiments of the present invention.

Device 300 includes a housing which holds syringes 310A-B in designated mounts. The housing may be fitted to hold specific size or sizes of syringes or may be suitable for syringes of a variety of sizes.

Optionally, device 300 is a handheld device sized and/or shaped to fit within the palm of one hand. Optionally, device 300 is a standalone device (i.e., not handheld), and/or integrated into another device. Optionally, the device is computer controlled. For example, device 300 is set to automatically inject and aspirate into a patient using a timer and/or at a pre-selected rate.

Optionally, device 300 is located on a base which is remote from a patient, and the needle in the patient is connected via tubes to the syringes. The device may be operated via flexible lumens (catheters and/or tubes) and/or a dual channel needle and/or cannula. In such case, one hand operation allows for stable hold and less damage may be caused by unintended movement during the use of the device, for example when treating joints or inner body cavities.

Figures 3B, 3C:
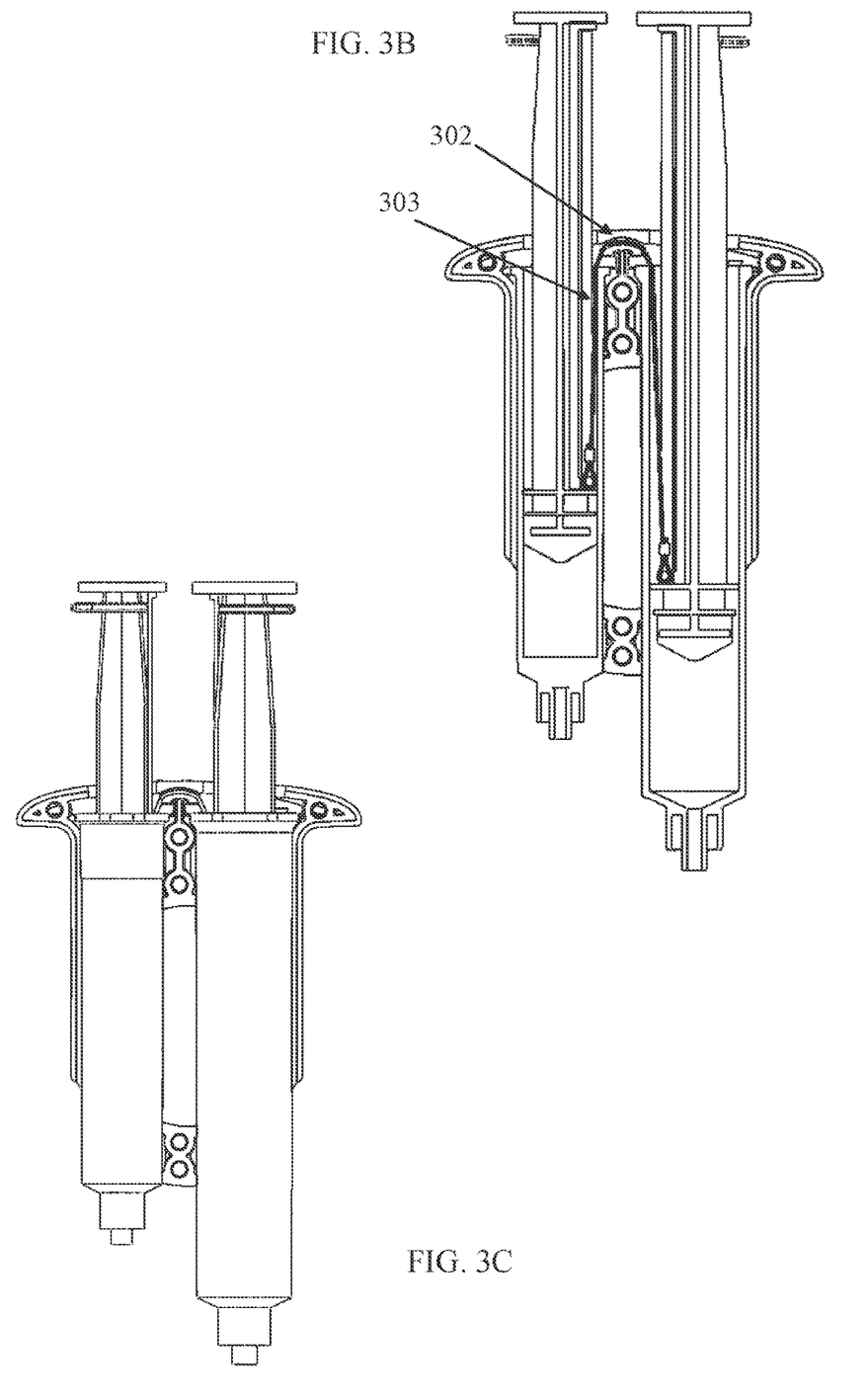

FIGS. 3B and 3C show cross sections of device 300. Anchor 302 is a hole molded in the structure of the housing. Flexible connector 303 is inserted into anchor 302.

Figure 3D:
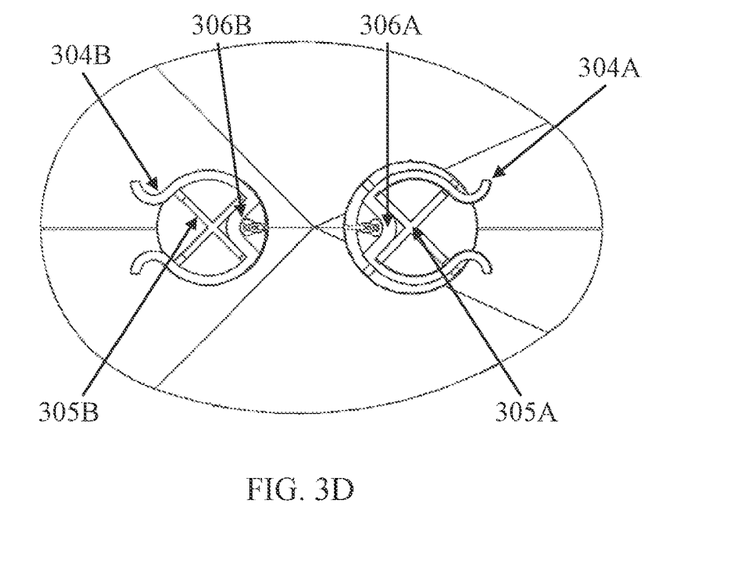

FIG. 3D shows a cross section of the upper part of syringes 310A-B. Holders 304A-B are clasps which are wrapping plungers 305A-B. Optionally, rods 306A-B are shaped to fit within X-shaped profile of plungers 305A-B. For example, rods 306A-B may have a profile with a 90 degrees angle (substantially triangular profile) which fits close to the center of the X shape.

Figure 3E:
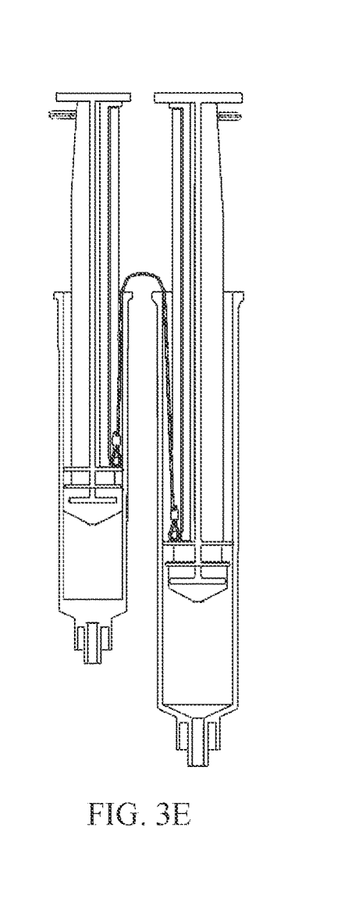
Figure 3F:
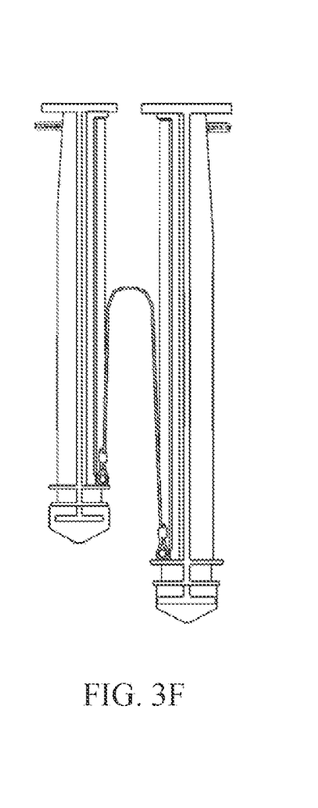
Figure 3G:
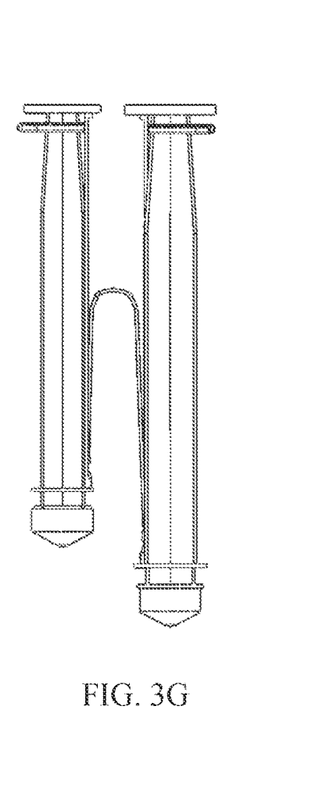

FIGS. 3E, 3F and 3G shows syringes 310A-B and plungers 305A-B.

Device 300 may include more than two syringes, for example by using more than one actuator, so one or more of the syringes are attached with multiple actuators.

Optionally, the housing is opened to inset syringes 310A-B. For example, the housing is made of two separable sections, which are attached by clasps and/or hinge(s).

Reference is now made to FIGS. 4A, 4B, 4C, 4D, 4E, 4F and 4G, which are illustrations of a device and an actuator for synchronized injection and aspiration having tubes and string, according to some embodiments of the present invention.

Figure 4A:
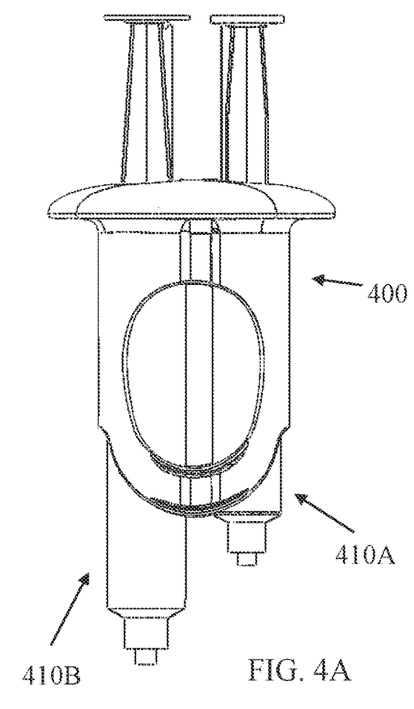
FIGS. 4A, 4B, 4C, 4D, 4E, 4F and 4G are illustrations of a device and an actuator for synchronized injection and aspiration having tubes and string, according to some embodiments of the present invention.
Figure 4B:
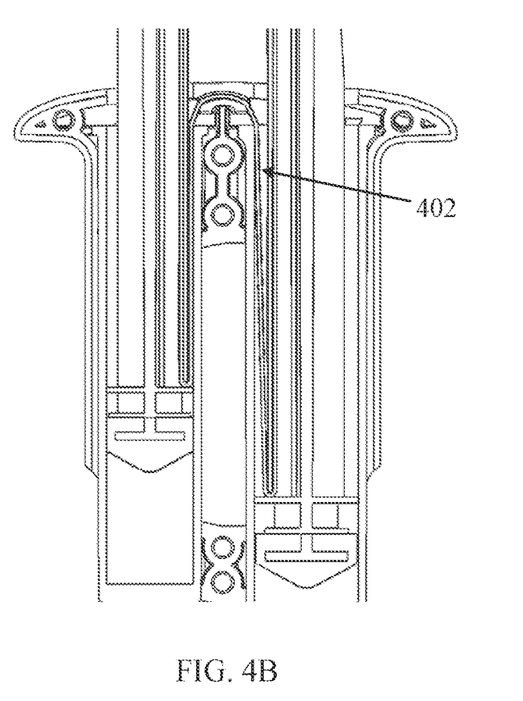
Figure 4C:
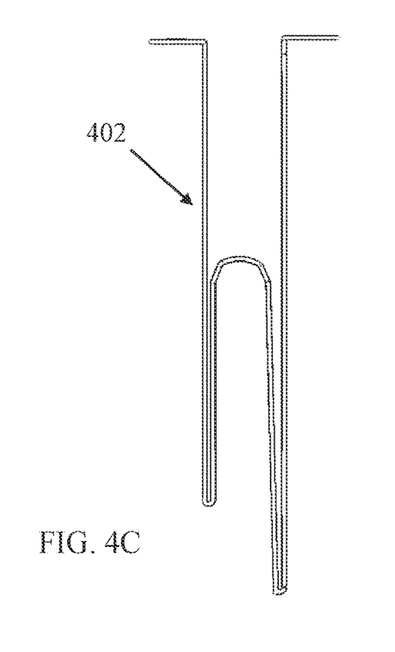
Figure 4D:
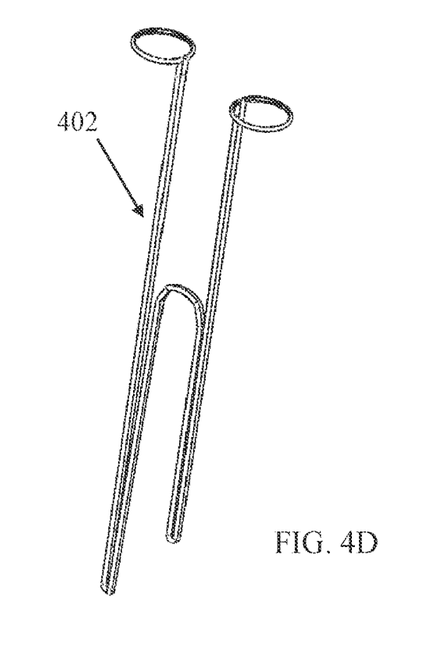
Figure 4E:
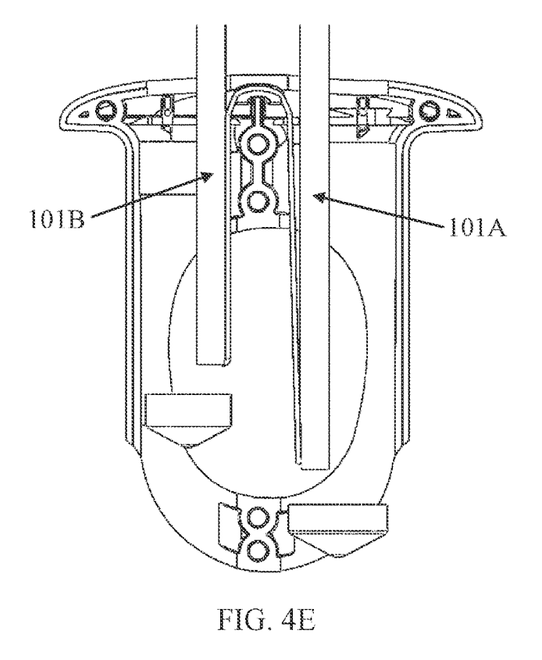
Figure 4F:
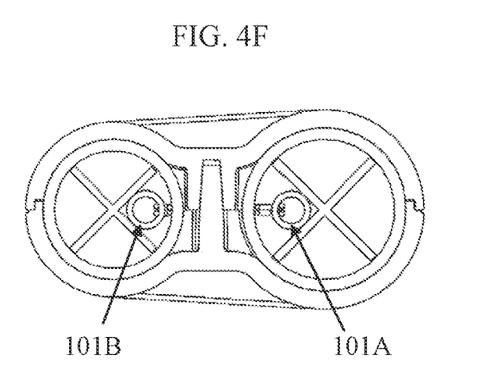

Device 400 includes an actuator in which the rods are tube 101A and tube 101B (shown in FIG. 4E), and the flexible connector is a string 402, which is inserted into tubes 101A-B and shown separately in FIGS. 4C and 4D. String 402 is connected to the proximal end of each of tubes 101A-B, goes inside tubes 101A-B and out of the distal end of each of tubes 101A-B. When syringe 110A is injecting, tube 101A is distally displaced and pulls string 402, which then proximally pushes tube 101B from the distal end, causing syringe 110B to aspirate.

Figure 4G:
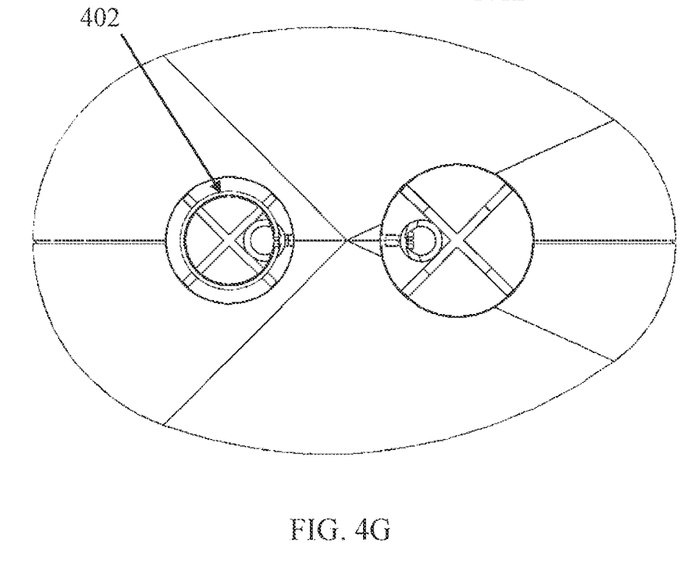

Optionally, as visible at FIG. 4G, the proximal ends of string 402 (exiting the proximal ends of tubes 101A-B) are held around the plungers of syringes 410A-B in a loop, for mechanical coupling to the plungers.

Optionally, the aspiration by syringe 110B is delayed after the injection by syringe 110A. This may be done by making flexible connector 102 loose when the injection by syringe 110A begins. Flexible connector 102 may be longer and/or may be connected to a more proximal part of rod 101A and/or rod 101B.

Figure 5A:
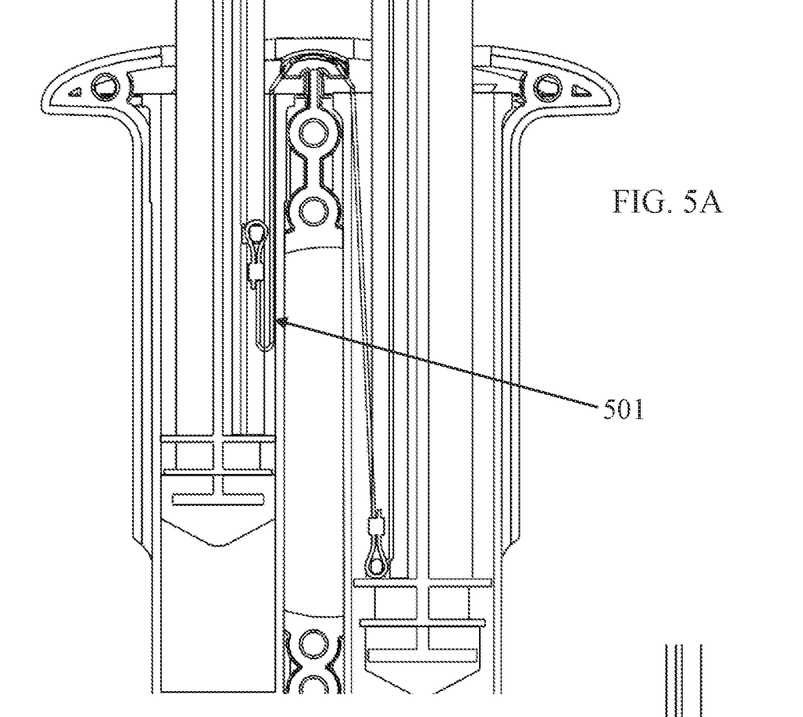
FIGS. 5A and 5B are illustrations of a device similar to the device of FIG. 2 and an actuator similar to the actuator of FIG. 3A respectively, having a loose flexible connector, according to some embodiments of the present invention.
Figure 5B:
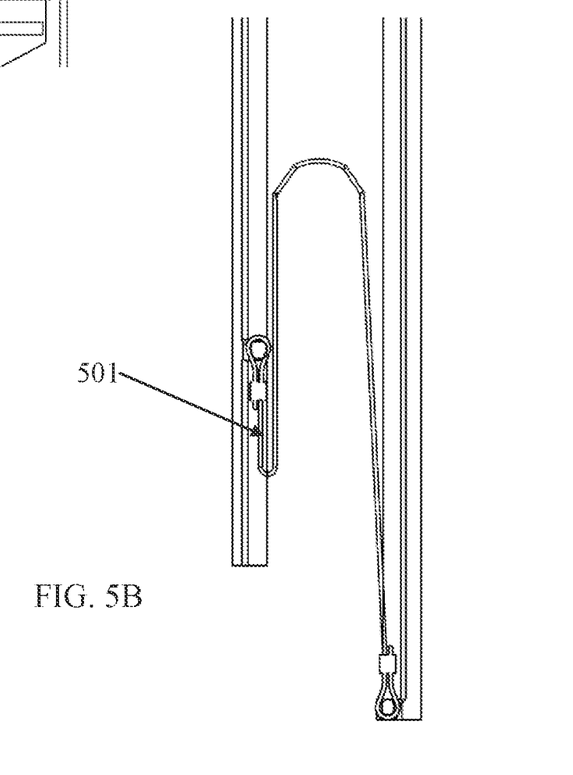

Reference is now made to FIGS. 5A and 5B, which are illustrations of a device similar to the device of FIG. 2 and an actuator similar to the actuator of FIG. 3A respectively, having a loose flexible connector, according to some embodiments of the present invention. Flexible connector 102 is connected to rod 101A at a distance from the distal end of rod 101A, thus creating a loose part 501 of flexible connector 102. When plunger 111A is pushed, loose part 501 is pulled and flexible connector 102 is stretched. When loose part 501 is gone, flexible connector 102 starts pulling rod 101B, which proximally displaces plunger 111B and resulting aspiration by syringe 110B.

Figures 6A, 6B:
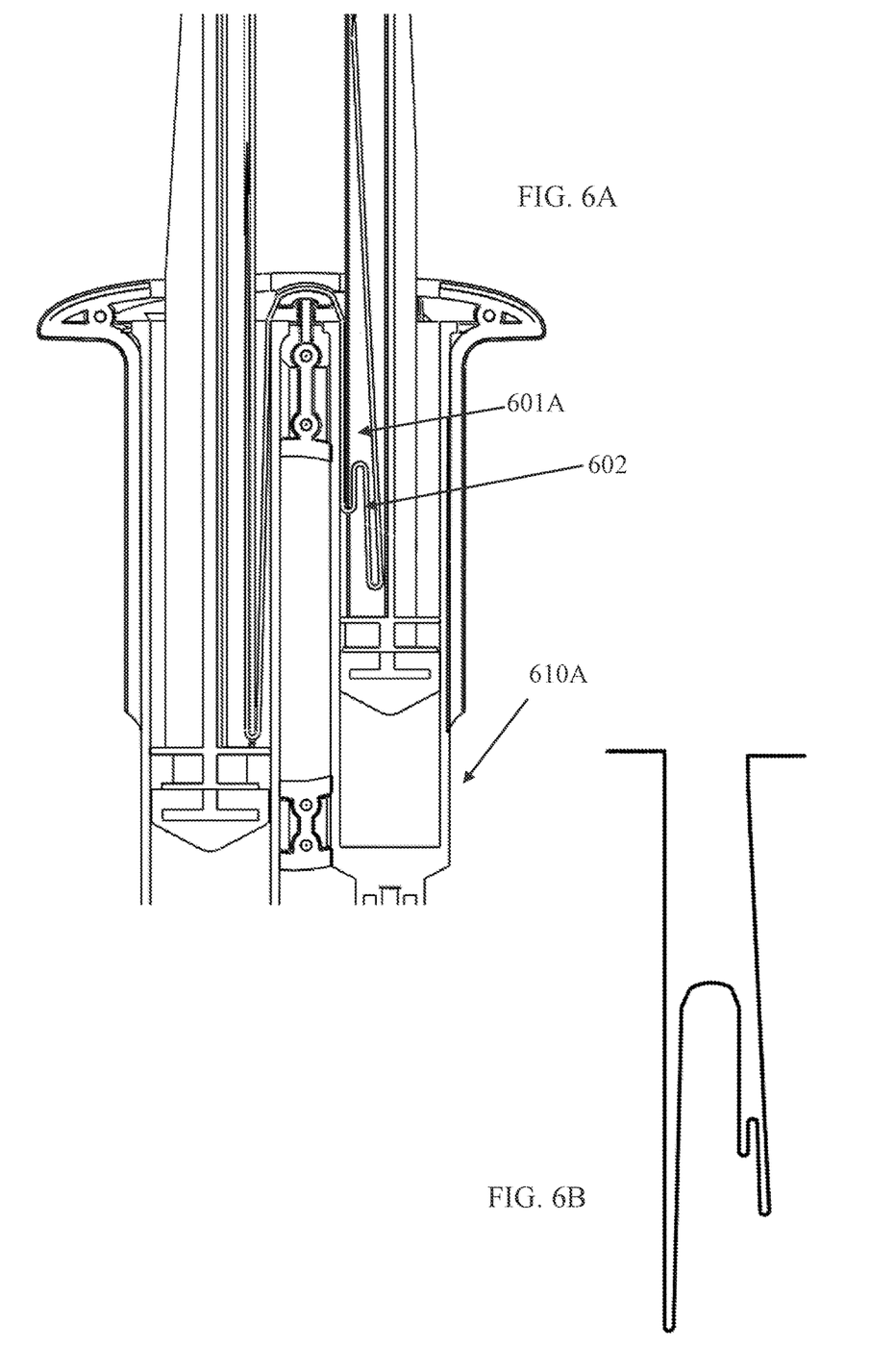
FIGS. 6A and 6B are illustrations of a device similar to the device of FIG. 4A with an actuator having tubes and string, according to some embodiments of the present invention.

Reference is now made to FIGS. 6A and 6B, which are illustrations of a device similar to the device of FIG. 4A with an actuator having tubes and string, according to some embodiments of the present invention. String 602 passes through a hole in tube 601A instead of the distal end of 601A, and therefore has a loose part when syringe 610A starts injecting.

Figure 7A:
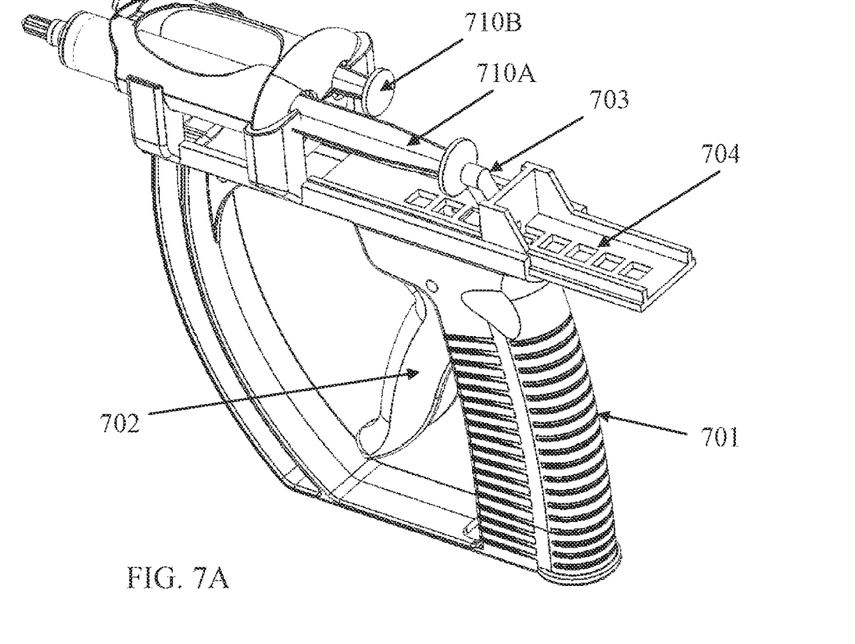
FIGS. 7A, 7B and 7C are illustrations and cross section of a pistol-shaped device for synchronized injection and aspiration, according to some embodiments of the present invention.
Figure 7B:
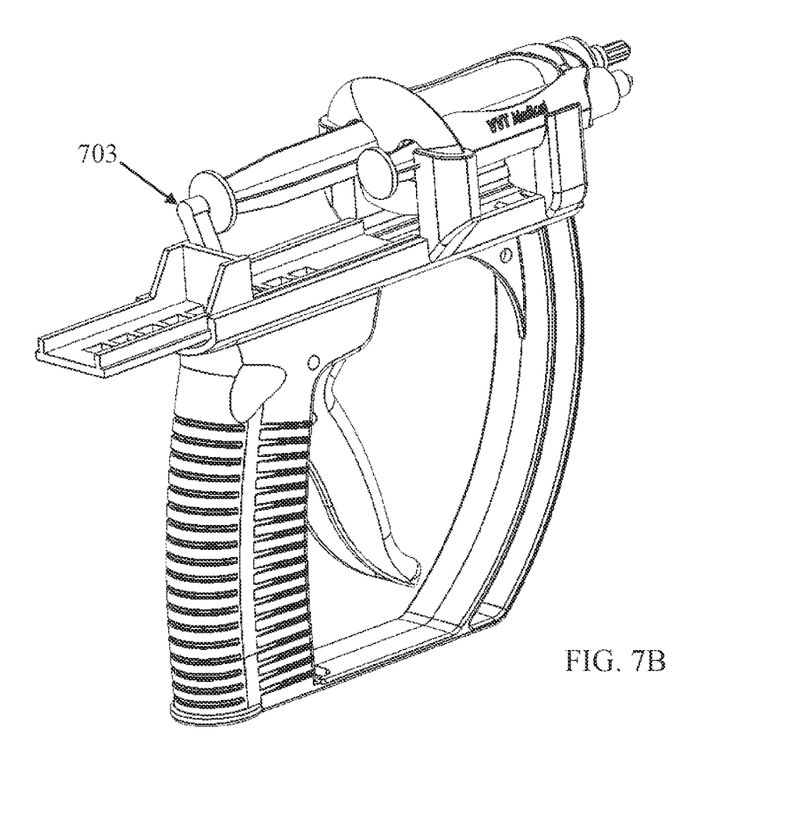
Figure 7C:
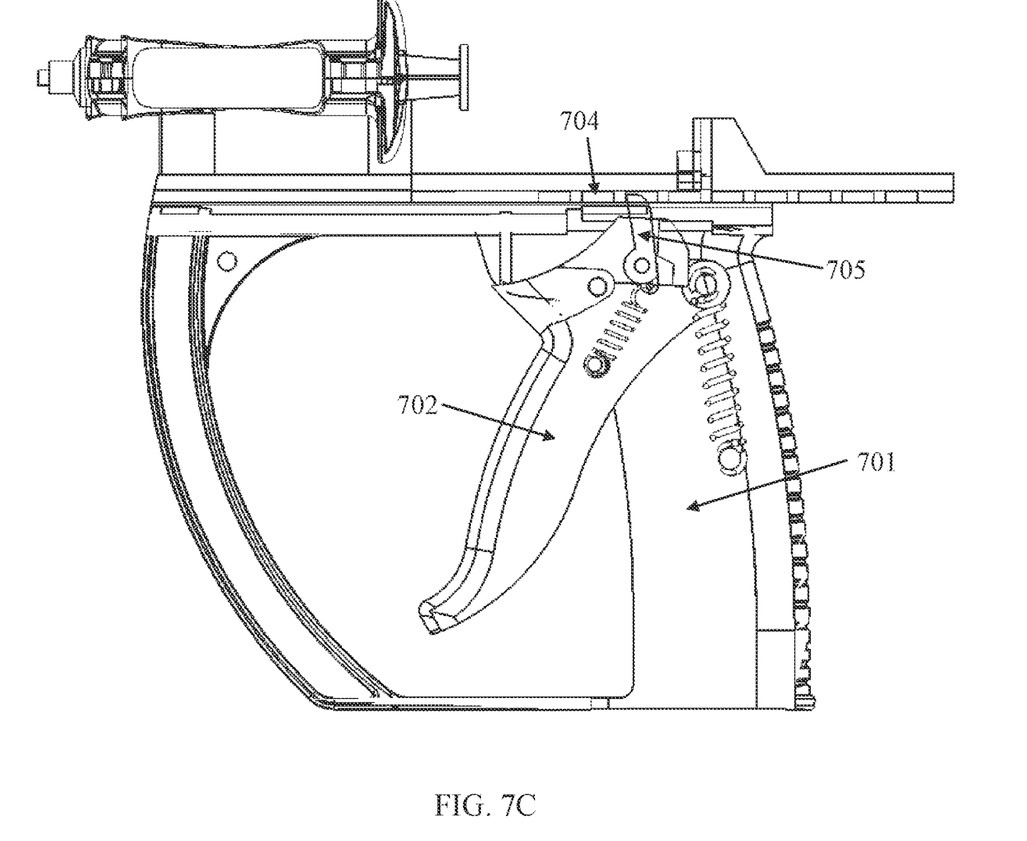

Reference is now made to FIGS. 7A, 7B and 7C, which are illustrations and cross section of a pistol-shaped device for synchronized injection and aspiration, according to some embodiments of the present invention.

Device 700 may include device 300 or device 400, which may be detachable from device 700. Device 700 may also include mount for directly inserting syringes.

Device 700 includes a grip 701 and a trigger 702. Trigger 702 is activates a pushing rod 703, which pushes plunger 710A. Optionally, trigger 702 is adjustable to push either plunger 710A or plunger 710B, for example by rotating over an axis.

Optionally, device 700 includes slots 704, in which a lever 705 is inserted. When trigger 702 is pressed, lever 705 is inserted into the next one of slots 704 and prevents pushing rod 703 from moving plunger 710A more than a specific distance. This allows controlled and equal amounts of fluid to be injection and aspiration each time trigger 702 is pressed.

Optionally, device 700 includes a display which presents information such as the number of times trigger 702 was pressed, the speed of pressing, the volume of fluid injected and/or aspirated, and/or any other information.

Figure 8:
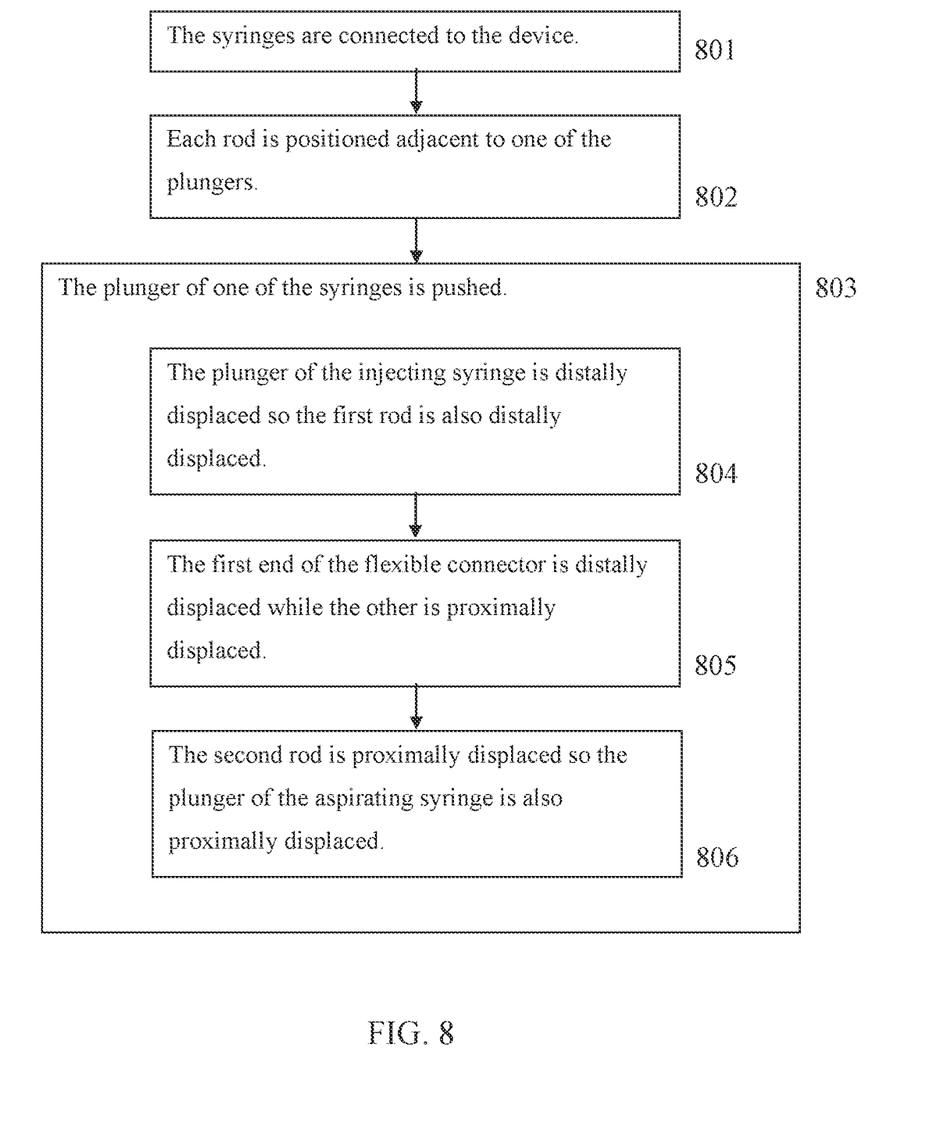
FIG. 8 is a flowchart schematically representing a method for using a device for synchronized injection and aspiration, according to some embodiments of the present invention.

Reference is now made to FIG. 8, which is a flowchart schematically representing a method for using a device for synchronized injection and aspiration, according to some embodiments of the present invention.

First, as shown at 801, the syringes are connected to the device, for example, by inserting them into the syringe mounts of the housing.

Then, as shown at 802, each rod is positioned adjacent to one of the plungers, so it is held between the head and the seal of the plunger.

Finally, as shown at 803, the plunger of one of the syringes is pushed. This activates synchronized injection and aspiration by the device:

First, as shown at 804, the plunger of the injecting syringe is distally displaced to inject fluid from the injecting syringe, so the first rod is also distally displaced.

Then, as shown at 805, the first end of the flexible connector is distally displaced by the first rod, while the other end of the flexible connector is pulled and is proximally displaced.

Finally, as shown at 806, the second rod is pulled by the other end of the flexible connector and is proximally displaced, so the plunger of the aspirating syringe is also proximally displaced to aspirate fluid from the aspirating syringe.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant syringes will be developed and the scope of the term syringe is intended to include all such new technologies a priori.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device comprising a housing fitted to hold standard-size syringes and an actuator for synchronized injection and aspiration, comprising:
   wherein the actuator comprises
   a first rod, having a length equal to an inner length between a head of a first plunger of a first standard-size syringe and a seal of said first plunger, and having a width smaller than a gap created between said first plunger and a barrel of said first standard-size syringe;
   a second rod, having a length equal to an inner length between a head of a second plunger of a second standard-size syringe and a seal of said second plunger, and having a width smaller than a gap created between said second plunger and a barrel of said second standard-size syringe;
   a flexible connector mechanically attached to a distal end of said first rod at a first end and to a distal end of said second rod at a second end;
   wherein the housing has syringe mounts for holding said first standard-size syringe and said second standard-size syringe and an anchor for supporting a distally disposed curve portion of said flexible connector and movement of said flexible connector, while said first plunger is pressed to inject fluid from said first standard-size syringe and the second standard-size syringe automatically and simultaneously aspirates fluid, enables single-hand operation.

2. The actuator of claim 1, wherein:
   said first rod includes a first holder at a proximal end, said first holder is detachably mechanically coupled to said first plunger; and
   said second rod includes a second holder at a proximal end, said second holder is detachably mechanically coupled to said second plunger.

3. The actuator of claim 1, wherein said first rod and said second rod are tubes, and said flexible connector is a string inserted into said tubes.

4. The actuator of claim 1, further comprising:
   a one-way mechanism which allows said flexible connector to move only in one direction.

5. The actuator of claim 1, wherein said first rod and said second rod have a profile with a 90 degree corner to fit within an X-shaped profile of the first and second plungers.

6. A device comprising the actuator of claim 1, further comprising:
   a grip; and
   a trigger coupled to a pushing rod which pushes said first plunger.

7. A method for enabling single-hand operation of standard-size syringes for synchronized injection and aspiration, comprising:
   placing first and second standard-size syringes in mounts of a housing fitted to hold standard-size syringes, the housing having an anchor for supporting a distally disposed curve portion of a flexible connector and movement of said flexible connector, while a first plunger in the first standard-size syringe is pressed to inject fluid from said first standard-size syringe and the second standard-size syringe automatically and simultaneously aspirates fluid, enables single-hand operation;

distally displacing a first plunger of the first standard-size syringe to inject fluid from said first standard-size syringe;

distally displacing a first rod, said first rod having a length equal to an inner length between a head of said first plunger and a seal of said first plunger, and having a width smaller than a gap created between said first plunger and a barrel of said first standard-size syringe;

distally displacing a first end of the flexible connector which is mechanically attached to a distal end of said first rod;

proximally displacing a second end of said flexible connector which is mechanically attached to a distal end of a second rod;

proximally displacing the second rod, said second rod having a length equal to an inner length between a head of a second plunger of the second standard-size syringe and a seal of said second plunger, and having a width smaller than a gap created between said second plunger and a barrel of said second standard-size syringe; and proximally displacing said second plunger to aspirate fluid from said second standard-size syringe.

8. A method of using a device for enabling single-hand operation of standard-size syringes for synchronized injection and aspiration, comprising:

inserting a first standard-size syringe and a second standard-size syringe into syringe mounts of a housing of said device, the housing having an anchor for supporting a distally disposed curve portion of a flexible connector and movement of said flexible connector, while a first plunger in the first standard-size syringe is pressed to inject fluid from said first standard-size syringe and the second standard-size syringe automatically and simultaneously aspirates fluid, enables simile-hand operation;

positioning a first rod adjacent to the first plunger of said first standard-size syringe, so said first rod is held by a head of said first plunger at a proximal end and by a seal of said first plunger at a distal end;

positioning a second rod adjacent to a second plunger of said second standard-size syringe, so said second rod is held by a head of said second plunger at a proximal end and by a seal of said second plunger at a distal end; wherein the flexible connector is mechanically attached to a distal end of said first rod at a first end and to a distal end of said second rod at a second end; and pushing said first plunger to inject fluid from said first standard-size syringe, while aspirating fluid from said second standard-size syringe.

* * * * *